United States Patent [19]

Henry

[11] 4,232,336
[45] Nov. 4, 1980

[54] INSPECTION OF ELONGATED MATERIAL

[75] Inventor: James W. Henry, Kingsport, Tenn.

[73] Assignee: Eastman Kodak Company, Rochester, N.Y.

[21] Appl. No.: 943,511

[22] Filed: Sep. 18, 1978

[51] Int. Cl.³ .............................................. H04N 7/18
[52] U.S. Cl. .................................. 358/106; 358/107; 358/903
[58] Field of Search .................. 358/107, 106, 93, 903

[56] References Cited
U.S. PATENT DOCUMENTS

| 3,714,372 | 1/1973 | Rosen | 358/107 |
| 4,136,950 | 1/1979 | Labrum | 358/107 |

Primary Examiner—Howard W. Britton
Attorney, Agent, or Firm—John F. Stevens; Daniel B. Reece, III

[57] ABSTRACT

Apparatus and method are described for inspecting elongated material such as strands, sheets, bundles or webs for the presence of surface irregularities, count of irregularities within a given length and angle of irregularities such as in the case of crimped fiber. A light source is used to form light areas and shadowed areas of the elongated material. A television camera produces a video signal of the light and shadowed areas and such signal is electronically analyzed with respect to number of alternating light and dark areas within a given length, and the relative widths of such light and dark areas, from which information can be obtained to confirm presence of irregularities, count or frequency, and angle.

10 Claims, 10 Drawing Figures

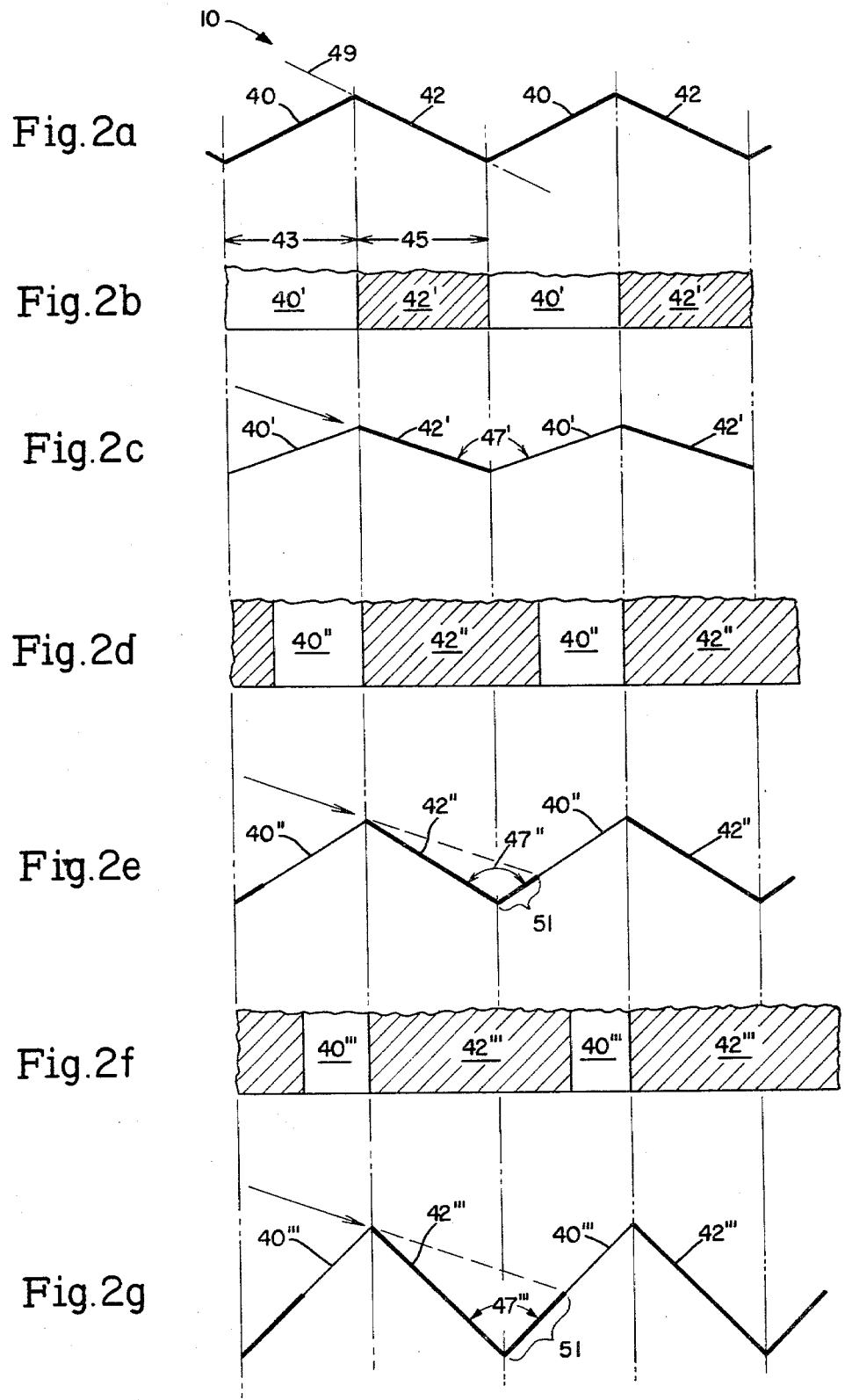

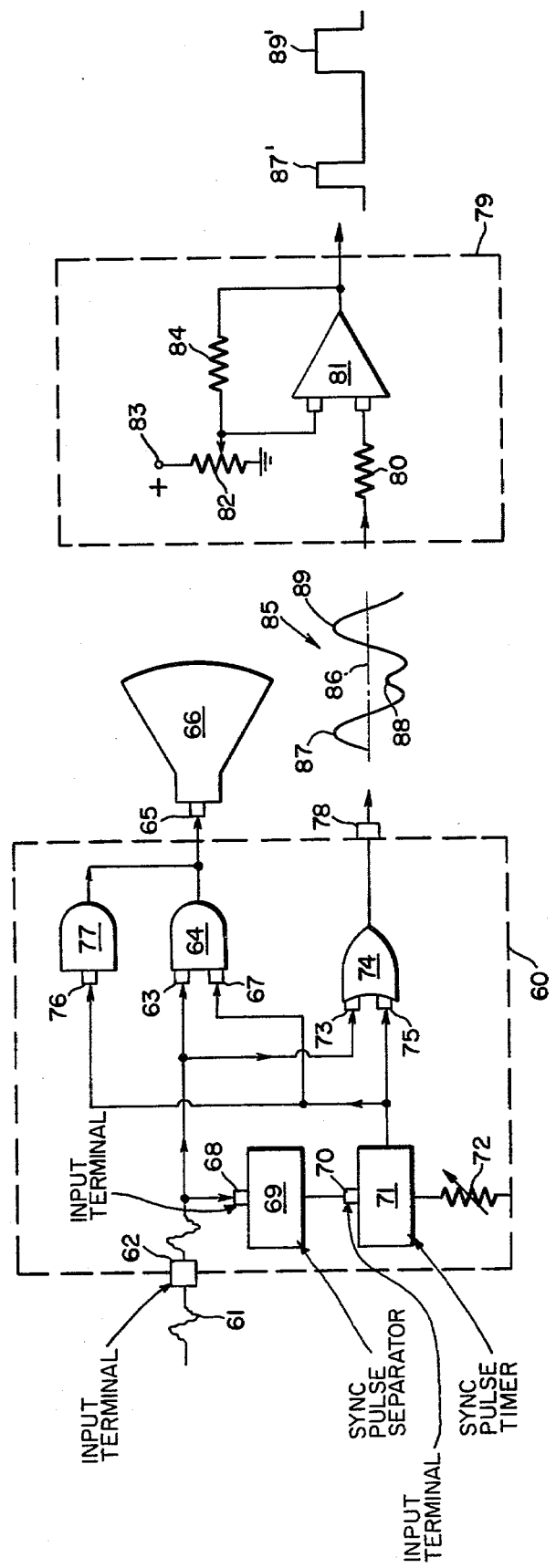

INSPECTION OF ELONGATED MATERIAL

BACKGROUND OF THE INVENTION

1. Field of the Invention

This invention relates generally to apparatus and method for inspection of elongated material. More specifically, this invention relates to apparatus and method for inspecting elongated material such as strands, sheets, bundles or webs for the presence of surface irregularities, count of irregularities within a given length, and angle of irregularities such as in the case of crimped fiber. Data obtained from such inspection may be used for quality control purposes.

This invention is particularly useful in monitoring production lines where continuous lengths of sheet or fibrous material is produced. Although various inspection uses will be apparent to those skilled in the art, the present invention will be described herein mainly in reference to the production of fiber tow which has been evenly crimped. Such fiber tow, e.g., cellulose acetate filter tow, is mechanically crimped for various reasons known to those skilled in the art. Due to factors beyond the control of the machines or their operators, however, sometimes there are lengths of the tow where crimp does not appear, or the frequency (count per unit length) or the degree of crimp is off specification. Such faults can be caused by improper mechanical adjustments or improper condition of the material being crimped. Loss of crimp, incorrect crimp pitch, or incorrect crimp angle in the material results in rejection of the material by customers and subsequent heavy losses to the manufacturer because of waste. The present invention provides a method and apparatus whereby such crimp may be continuously monitored, and if faulty conditions are detected, the appropriate steps can be taken before substantial loss results. Furthermore, such detection systems can be designed so that a plurality of production lines may be alternately monitored from a central location.

2. Description of the Prior Art

Various electronic systems are presently known for detecting defects in continuous lengths of material. For example, U.S. Pat. No. 3,584,225 relates to a yarn inspection device which uses optical devices and electronic circuitry to detect defects in yarn. U.S. Pat. No. 3,114,797 relates to a television system for detecting differences or changes in shape, size, color, intensity or texture. Such differences or changes are detected by comparing a scene at one instant with an image produced from the same scene after a time delay. U.S. Pat. No. 3,700,903 relates to detection systems wherein a coherent light beam is used to scan the surface of an object in a repetitive pattern. An output signal is produced by light reflected from the object for determining characteristics of the surface of the object.

The present invention provides apparatus and method for continuously monitoring continuous lengths of material, for detecting surface irregularities, obtaining data from such irregularities, and converting such data into useful information. While the prior art shows the detection of surface defects or differences, this is often not sufficient information for adequate quality control and applicant's invention provides for obtaining useful information from irregularities such as count and shape.

SUMMARY OF THE INVENTION

The present invention provides apparatus and a method for obtaining information from an advancing continuous length of material by (1) moving the material along a predetermined path, (2) positioning a stroboscopic light source adjacent the path of the material so as to direct its light at an angle relative to the material such that surface variations thereof will make a pattern of light and shadowed areas, (3) positioning a television camera adjacent the path of the material such that the illuminated portion of the material will be in its field of view, (4) generating an electrical pulse at selected intervals to activate the light source for a predetermined length of time and to trigger the scanning of a frame by the television camera, (5) converting the image of the frame developed by the television camera into a video signal, (6) electrically applying the video signal to the input of a separator circuit which is adapted to produce a control pulse on its output terminal of predetermined duration for each horizontal synchronization pulse contained in the video signal, (7) electrically applying the video signal and the control pulse from the separator circuit to separate input terminals of a gate adapted to pass the video signal through to its output terminal whenever the control pulse is applied to the second input terminal, (8) electrically applying the output signal from the gate to a comparator for converting all pulses of greater than a predetermined amplitude contained within the passed video signal into a digitized signal, and (9) feeding the digitized signal into a digital computer for further processing.

Such method and apparatus provide a convenient and reliable means for monitoring production lines to obtain physical data therefrom which can be electronically processed as a quality control measure.

BRIEF DESCRIPTION OF THE DRAWINGS

FIG. 2a is an elevation views of crimped fiber tow. FIGS. 2b through 2g are elevation and plan view, shown diagrammatically, of fiber tow crimped at different angles, and the direction of light beam from the stroboscope.

FIG. 4 is a circuit diagram of the video analyzer and signal comparator.

DETAILED DESCRIPTION OF THE INVENTION

To insure uniformity of the tow, it is necessary to maintain the presence of crimp, a particular crimp count or frequency for a given length of tow, and/or crimp angle. The present invention provides a method and apparatus for detecting absences of crimp in the tow, the number of crimps per unit length, and the crimp angle.

Figure 1:
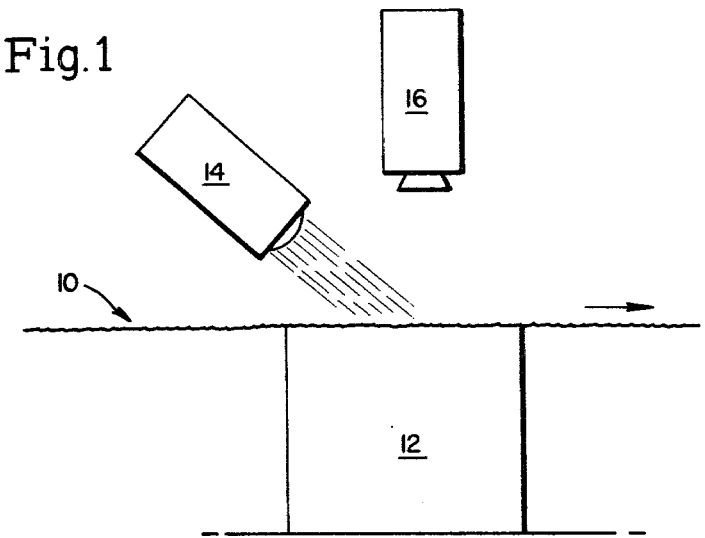
FIG. 1 is a partial schematic elevation view illustrating a preferred arrangement of elongated material, television camera, and stroboscope.

Referring to FIG. 1, irregular filamentary material, e.g., a continuous band of crimped fiber tow 10, is fed over support 12 in the direction indicated. For the sake of simplicity, the filamentary material will be hereinafter referred to as tow. The tow generally moves at a rapid rate, for example, about 20 feet per second, but, of course, the speed may be much slower or much faster. Support 12 may be placed in a convenient position anywhere along the path of the crimped tow in various conventional operations well known in the art, or may be a separate inspection operation.

Stroboscope 14 is positioned adjacent the band of tow 10 so as to illuminate a portion of tow 10 as it passes over support 12. Stroboscope 14 is positioned at an angle relative to the direction of movement of tow 10 as shown in FIG. 1 to create a pattern of alternate light and dark strips on the tow as described hereinafter. Television camera 16 is placed in close proximity to stroboscope 14 in a manner such that the pattern of light and dark strips created by the light on the crimped tow will be in its field of view. Preferably, camera 16 is aimed substantially directly at a generally linear section of the tow. Also, the stroboscope 14 is directed towards the tow at an angle such that the generally parallel rays of light are substantially parallel to the tow sections 42 at the maximum anticipated crimp angle.

Figure 3:
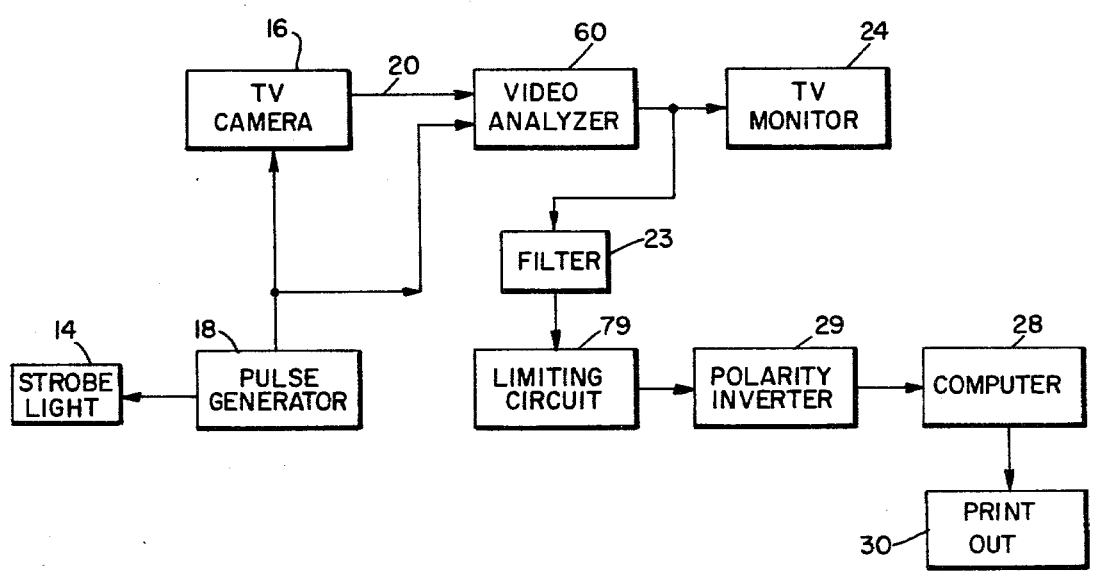
FIG. 3 is a diagram of the electrical components used in this invention.

As shown in the diagram of FIG. 3, the television camera 16, the synchronization pulse of which is controlled by the pulse generator 18, feeds its video signal into a video analyzer system 60. The electrical signal from video analyzer 2 is fed to a television monitor 24 and preferably to a filter 23 prior to being fed to a limiting circuit 79 which reshapes the waveform, then through a polarity inverter 29 which feeds square wave impulses into computer 28, which is preferably connected to print-out machine 30. Coordination of television camera 16 and stroboscope 14 is maintained by pulse generator 18.

FIGS. 2b and 2c are diagrammatic sketches illustrating in somewhat simplified form the section of tow shown in FIG. 2a. FIG. 2b illustrates the principals involved in creating light and dark strips on a section of tow by directing a beam of light at an angle to the crimp. Preferably the beam of light is collimated in at least one plane, i.e., the plane of the paper. Light from the direction illustrated by the arrow creates light strips 40 and dark strips or shadows 42 on the crimped tow 10. These alternating light strips 40 and dark strips 42 are detected by television camera 10 and appear in the video signal developed by camera 10. Also, the width 43 and 45 of the strips which appear in FIG. 2c, for a predetermined crimp size, is a function of crimp angle 47 which can be determined mathematically by computer by well known means.

In practice, crimped tow normally will not have sharply defined angles and absolutely flat sections from the angles. Actually, the tow may appear somewhat wavy as shown in FIG. 2a. The light would thus be directed substantially parallel the side 42 sloping away from the light, i.e., parallel to a line 49 which is tangent to the bends in the tow.

FIGS. 2b through 2g illustrate the relationship between the width of the strips and the crimp angle. FIGS. 2b and 2c illustrate the light rays (arrow) parallel to side 42' at the maximum anticipated crimp angle 47'. FIGS. 2d and 2e illustrate a slightly decreased angle 47" at which time the light strips 40" get smaller and dark areas 42" get larger because of the shadow 51 cast on side 40'. In FIGS. 2f and 2g, angle 47''' has decreased even more, casting a longer shadow 51, thus making the light strips 40''' even smaller and the dark strips 42''' even larger. As will be apparent to those skilled in the art, a direct relationship exists between the number of strips for a given length of tow and crimp count, and a direct relationship exists between the width of dark strip relative to width of light strip and the crimp angle. Such relationships may be programmed on a computer for obtaining numerical data by those skilled in the art.

The number of alternating light strips and shadow strips per unit length, and the relative width of such strips is therefore transformed into a video signal for analysis.

The video signal from the television camera is processed by a system shown diagrammatically in FIG. 3. The television camera 16 is synchronized as to frame rate and scanning rate by synchronization generator 18. The vertical synchronization pulse from generator 2 is used to trigger stroboscopic light source so that at the beginning of each field scan a pulse of light is triggered to light the tow band. The image reflected through the camera lens to the sensitive vidicon tube is stored in the tube and is read out by the scanning electron beam which generates the video signal. Because of the extremely short pulse of light, the image stored on the tube is not blurred due to movement of the tow. The video signal from the camera 16 is transferred to a video analyzer 60 where a selected group of luminance signals along a line perpendicular to the scanning lines of the picture are analyzed and presented as a slow scan video signal. The composite picture of the full television frame with an added graphic display of the slow scan video signal is shown on a television monitor 24. The slow scan television signal (e.g., about 525 lines and about 30 frames per second) is fed to a limiting circuit 79 and converted to a square wave representation of the signal in which frequency is converted to pulse rate and wave length to pulse duty cycle. These pulses are analyzed for frequency and duty cycle by computer 28 which calculates the crimp frequency (or count) and crimp angle, and presents it as a printout on printer 30.

The video signal from the television camera 16 may be processed and fed into a digital computer to obtain numerical data. A system for such processing is shown in FIG. 4. The video signal is fed to a video analyzer system 60 where it is displayed on a kinescope monitor 66 while selected parts thereof are simultaneously displayed as a line on the kinescope monitor and preferably fed through a filter to an analog signal comparator system. The output signal from video analyzer system 60, having the simulated waveform illustrated in FIG. 4, is filtered and shaped, generally into the form illustrated, so that it is suitable for feeding into a digital computer (not shown). Pulses from the analog signal comparator system are fed to the digital computer which is programmed to arrange them into useful information using count and pulse widths.

It is preferred in most instances to display the video signal on a kinescope monitor 66. Obviously, however, such display is not necessary for processing the video signal to be fed into a digital computer.

The video signal produced by a standard television camera is an electrical signal characterized by a content of electrical alternating wave frequencies ranging from 30 hertz to as high as 35 megahertz. The amplitude of the waves contained within this band of frequencies defines the brightness of the portion of the television picture associated with the wave. The frequency defines the size of the picture element associated with the wave portion. High amplitudes represent bright picture elements. High frequencies represent small picture elements.

In digital analysis of a picture, the brightness of the image can be reduced to a binary number in which presence of a signal above a minimum level represents a shadow being present, and lack of such a shadow is represented by a signal which falls below the minimum level. In digital logic parlance, presence of a shadow is defined as a 1. Absence of a shadow is defined as a zero. Simplification of the signal description relative to amplitude conditions to a 1 or zero state makes possible the elimination of complicated electronic circuits capable of handling the wide range of signals which are required to synthesize a complex wave form which would normally describe the presence of a shadow.

The operation of the video analyzer system 60, which is designed to convert the video signal received from a standard television camera into a waveform suitable for being introduced into an limiting circuit 79, may be described as follows.

The video signal 61 from the television camera 16 is applied through a suitable electrical input terminal means 62 to the first input terminal 63 of a NOR gate 64. The output of the NOR gate is electrically connected to the input terminal 65 of a kinescope monitor system 66. Thus, so long as no control signal is present at the second input terminal 67 of the NOR gate 64, the video signal 61 applied to terminal 63 is passed through the gate to and is displayed on the kinescope monitor 66.

The video signal 61 from the television camera is also simultaneously applied via input terminal means 62 to the input terminal 68 of a suitable horizontal synchronization pulse separator circuit 69. Each horizontal synchronization pulse contained in the video signal 61 is detected by this circuit and, after being suitably reshaped, is applied as a trigger pulse from the output of circuit 69 to the input terminal 70 of a synchronization pulse timer circuit 71. Circuits 69 and 71 may be contained in a single unit, if desired.

The trigger pulse from circuit 69 starts the running of the synchronization pulse timer circuit 71, which is designed to produce a single control pulse at its output terminal of a predetermined duration for each trigger pulse received. An adjustable potentiometer 72 is electrically connected to circuit 71 and is used to adjust the point in time when the leading edge of the control pulse appears on the output terminal of the circuit in relationship to the time at which the leading edge of the trigger pulse appeared at the input terminal 70 of the circuit.

The first input terminal 73 of an AND gate 74 is electrically connected directly to the input terminal 62. The sound input terminal 75 of the AND gate 74, as well as the second input terminal 67 of NOR gate 64, is electrically connected to the output terminal of the synchronization pulse timer circuit 71. Preferably, amplifier circuit 77 is used in connection with this invention. However, the amplifier circuit 77 may be omitted if desired. If used, the input terminal 76 of an amplifier circuit 77 is also electrically connected to the output terminal of circuit 71.

As the leading edge of the control pulse from the synchronization pulse timer circuit 71 appears on the second input terminal 67 of NOR gate 64, it turns this gate off thereby removing the video signal from the kinescope monitor circuit 66. Simultaneously, the leading edge of the control pulse appears at the input terminal 76 of the amplifier circuit 77 wherein it is processed and applied through the output terminal of this circuit to the input terminal 65 of the kinescope monitor 66. This results in part of a vertical line being produced on the face of the kinescope which is the width of the control pulse and is positioned on the kinescope face in accordance with when the control pulse is generated in reference to the horizontal synchronization pulse. Once the trailing edge of the control pulse passes, the NOR gate 64 is turned back on and the output from amplifier circuit 76 terminates.

When the leading edge of the control pulse from the synchronization pulse timer circuit 71 is applied to the second input terminal 75 of AND gate 74, the gate is turned on thereby passing the video signal from input terminal 62 to the output terminal 78 of the video analyzer system 60. This passing of the video signal through AND gate 74 will continue so long as the control pulse is present at input terminal 75.

As will be appreciated, through the use of this video analyzer system, the face of the kinescope monitor circuit will display the picture being picked up by the television camera plus a vertical line that represents the position and portion of the video signal that is being passed through AND gate 74 to the analog signal comparator circuit 79. Thus, a line selection is provided wherein one sample of a predetermined width is taken at a preselected point in each horizontal sweep line of the kinescope. This sample, combined with the others so taken, forms a vertical line or row. The preselected point at which the samples are taken, and therefore the position of the vertical line formed by the samples, can be electrically positioned to any point on the kinescope face by adjusting potentiometer 72. The sampled output appearing at output terminal 78 of the video analyzer system 60 is in a form suitable for being fed directly into the analog signal comparator circuit 79.

Video analyzer systems, as described generally above, are commercially available. For example, Video Analyzer 301 and Video Analyzer 302 are available from Colorado Video, Incorporated, of Boulder, Colorado.

In the processing of television signals derived from a monitor system, signals may be produced by the presence of areas of light and dark due to the shadowing illumination produced by a light source positioned to reveal the presence of crimp folds by low angle illumination. As a result of poor illumination uniformity, areas of light and dark may be present in the picture area, and these areas produce signals which add algebraically to the desired signal produced by the crimp to produce excursions in signal level which are frequently greater than the amplitude of the signal produced by the crimp pattern. The excessively strong signal may overpower any threshold devices which may be inserted into the signal processing chain to establish a baseline for the normal alternating wave pattern produced by a crimp pattern. The wide excursions caused by unwanted signals will drive a composite television (consisting of video and synchronization pulses) signal past the threshold level, resulting in a condition where the desired signal is either above or below the threshold level and unavailable for analysis since the function of the threshold device is to clip or limit the normal alternating wave form so that it possesses a square wave or pulse form after processing. The net effect of the additional excursion in the wave form is to push the desired information past the threshold limits, thereby wiping out the desired signal information.

The video signal may be processed to remove the synchronization signals, then to remove the interfering low frequency signals because of uneven illumination of the picture and uneven response from the television camera sensitive camera tube. These synchronization and interfering low frequency signals (about 30 Hz to about 300 Hz) may be removed by filters known to those skilled in the art. One suitable filter is described in my patent application filed of even date herewith entitled "Signal Filter", incorporated herein by reference, wherein apparatus is described for removing low frequency signals by summing their integral with the original input signal. An integrator is adjusted to follow the excursions of undesired low frequency signals but not the faster excursions of the desired signal. The algebraic sum of the integrator output and the input signal contains only the desired signal since the amplitude of signal left after the sum of the integral and input signal is completed contains a negligible amount of the undesired signal. The system perfects the television signal for further processing by counters and computers, thereby making a television crimp monitor system reliable and feasible in cost.

The video signal taken from the output terminal 78 of the video analyzer system 60, representing a slow-scan video signal showing the luminosity of points sampled along a vertical line which intersects each of the scanning lines of the video picture, is preferably fed through the filter mentioned above and into the analog signal comparator circuit 79. A typical example of such a circuit is shown although other circuitry for accomplishing this function will be apparent to those skilled in the art. The video signal is fed through a resistor 80 to an analog signal comparator 81. The comparator (type LM 311 manufactured by Intersil Corporation) delivers a digitized signal only if the introduced signal exceeds the level of a threshold voltage taken from a power source, such as shown by variable potentiometer 82. The excitation of the potentiometer is taken from a suitable direct current power supply 83 which also serves as excitation for the comparator circuit. A feedback loop including a resistor 84 connects the output of comparator 81 to threshold input signal. This resistor defines the sensitivity of the comparitor to signal differences.

A portion of the video signal from output terminal 78 of the video analyzer system 60 being electrically applied to the analog signal comparator circuit 79 is illustrated at 85. The threshold voltage set by the adjustment of potentiometer 82 is indicated by broken line 86. Signals of varying strengths which represent various light and dark areas viewed by the television camera are depicted as pulses 87 through 89. As is apparent, the amplitude of these pulses varies depending on the brightness of the target being viewed while the width of the pulse is proportional to the duration of the target in the part of the camera's viewing area.

When the leading edge of a pulse, such as pulse 87, rises above the threshold voltage setting 86, the analog signal comparator circuit 79 is turned on and produces the leading edge of an output pulse, such as pulse 87'. When the trailing edge of the pulse 87 falls below the threshold voltage setting, the analog signal comparator circuit 79 is turned off thereby terminating pulse 87'. This pulse generating process is repeated with each video signal pulse in pulse train 85 that exceeds the predetermined setting of the threshold voltage level 86.

As will be apparent, video input pulses that do not exceed this threshold voltage level, such as pulse 88, will not activate or turn on the analog signal comparator circuit 79 and thus will not appear in the output pulse train.

Pulses from the analog signal comparator circuit 79 are then fed in a conventional manner to a digital computer, which uses the count and width of the pulses to provide numerical information on elongated material moving through the television camera's field of view.

The square wave signal produced as described above, or by other means such as amplification in a limiter amplifier to the point where wave squaring is effected, or by shaping in a diode clipping circuit, is well suited for introduction to the input system of conventional electronic digital counters such as, for example, the series manufactured by the Hewlett-Packard Company and marketed under the series number 5300. The square wave produced by analog signal comparitor 79 is introduced to the counter. The counter registers one count of each square wave introduced to it.

In addition to the simplified means of producing a signal suitable for introduction to a computer, an analog-to-digital converter system which translates the gray scale of the video image into a digital code and stores it in the computer memory may be used. Once in memory, the computer is programmed to accept digital codes representing a level above the threshold established, and to reject those codes representing levels below the threshold. A count of the acceptable codes is made and the time during which the code is received recorded. One count is recorded for each time the code is received. The count is distributed in the record according to the time duration of the code received. A single video frame representing 1/30 second of time is digitized by the analog to digital converter and entered into the computer memory.

This invention will be further illustrated by the following example although it will be understood that this example is included merely for purposes of illustration and is not intended to limit the scope of the invention.

EXAMPLE

A Cohu television camera type 4400 is installed over a running tow line in which crimp is present in the tow. A General Radio stroboscopic lamp accepting the 60 Hz vertical synchronization pulses from a Cohu television synchronization generator is installed to illuminate the area of tow covered by the camera lens. A Colorado Video Model 301 video analyzer is supplied with video signal from the camera and, in turn, supplies a composite video picture signal and a slow scan signal to a 14-inch television monitor. The slow scan video signal is also supplied to a system consisting of an operational amplifier with a gain of 10X, feeding into a high pass filter with a roll-off beginning at 400 Hz, decreasing to 200 Hz (50% response) to 60 Hz (5% response). The output of this filter is again amplified with an operational amplifier (gain 10X) and the output supplied to a type LM 311 operational amplifier comparitor adjusted in circuit parameters to serve as a limiter and square wave shaping device. The output of this limiter is supplied to TTL gates and from these gates to a microprocessor programmed to determine the crimp count and crimp angle. The microprocessor supplies signals to a printer for hardcopy printout of the processed crimp information. The system is found to produce reliable crimp information concerning the tow running under the television camera. It is found that a large degree of random crimp is present in the tow. Upon departure from normal standard crimp conditions, the alarm system incorporated in the microprocessor is activated to produce a lamp and audio alarm to the operator.

The invention has been described in detail with particular reference to preferred embodiments thereof, but it will be understood that variations and modifications can be effected within the spirit and scope of the invention.

I claim:

1. The method of inspecting elongated material such as strands, sheets, bundles or webs for surface variations which comprises the steps of
    (a) moving said elongated material along a predetermined path,
    (b) positioning a stroboscopic light source adjacent the path of said elongated material so it will direct its illumination at an angle relative to said elongated material causing surface variations thereof to make a pattern of light and shadowed areas,
    (c) positioning a television camera adjacent the path of said elongated material such that the illuminated portion of said material will be in its field of view,
    (d) generating an electrical pulse at selected intervals to activate said light for a predetermined length of time and to trigger the scanning of a frame by said television camera,
    (e) converting the image of the frame developed by said television camera into a video signal,
    (f) electrically applying said video signal to the input of separator circuit means which is adapted to produce a control pulse on its output terminal of predetermined duration for each horizontal synchronization pulse contained in said video signal,
    (g) electrically applying the video signal and the control pulse from the separator circuit means to separate input terminals of gate means adapted to pass said video signal through to its output terminal whenever said control pulse is applied to said second input terminal,
    (h) electrically applying the output signal from said gate means to comparator means for converting all pulses of greater than a predetermined amplitude contained within said passed video signal into a digitized signal, and
    (i) using the digitized signal as a source of information in the inspection of said elongated material.

2. The method according to claim 1 wherein at least the portion of the path of elongated material illuminated by said stroboscopic light source is substantially linear.

3. The method according to claim 1 wherein the elongated material is fiber tow having a generally regular crimp.

4. The method according to claim 3 wherein the stroboscopic light source provides a beam of light collimated in at least one direction and positioned such that the rays thereof are substantially parallel to one slope of the crimped tow at the maximum anticipated crimp angle.

5. The method according to claim 1 wherein interfering, relatively low frequency signals are filtered from the video signal.

6. The method according to claim 1 which includes electrically applying the video signal and the output of said separator circuit means to the input of a second gate which is adapted to pass the video signal through to its output terminal whenever the control pulse is absent from said second input terminal, and electrically applying the output of said second gate to a kinescope monitor to display said video signal.

7. Apparatus for inspecting elongated material such as strands, sheets, bundles or webs for surface variations comprising
    (a) means for moving said elongated material along a predetermined path,
    (b) a stroboscopic light source positioned adjacent the path of said elongated material so as to direct its illumination at an angle relative to said elongated material to cause surface variations thereof to make a pattern of light and shadowed areas,
    (c) a television camera positioned adjacent the path of said elongated material such that the illuminated portion of said material will be in its field of view,
    (d) means for generating an electrical pulse at selected intervals to activate said light for a predetermined length of time and to trigger the scanning of a frame by said television camera,
    (e) separator circuit means adapted to produce a central pulse on its output terminal of predetermined duration for each horizontal synchronization pulse contained in the video signal produced by said television camera,
    (f) gate means having a first input terminal electrically connected to said video signal and a second input terminal electrically connected to said output terminal of said separator circuit means, said gate means being adapted to pass video signal through to its output terminal whenever said central pulse is applied to said second input terminal,
    (g) comparator means connected to said output terminal of said gate means for converting all pulses of greater than a predetermined amplitude contained within said passed video signal into a digitized singal, and
    (h) means for counting the pulses in said digitized signal to derive useful information therefrom.

8. Apparatus according to claim 7 wherein a second gate having a first input terminal electrically connected to said video signal and a second input terminal connected to said output terminal of said separator circuit means, said second gate means being adapted to pass said video signal through to its output terminal whenever said control pulse is absent from said second input terminal, and a kinescope monitor electrically connected to said output terminal of said second gate means for displaying said video signal.

9. Apparatus according to claim 8 wherein said output terminal of said separator circuit means is connected to said output terminal of said second gate means whereby said control pulse appears as a vertical line on said kinescope monitor.

10. Apparatus according to claim 8 which includes amplifier circuit means for the control pulse being applied to said kinescope monitor.

* * * * *